(12) United States Patent
Le Strat et al.

(10) Patent No.: US 8,217,152 B2
(45) Date of Patent: Jul. 10, 2012

(54) PROCESS FOR THE PURIFICATION OF IL-18 BINDING PROTEIN

(75) Inventors: Claire Le Strat, Les Monts de Corsier (CH); Frederic Meuwly, Lausanne (CH); Pierre Wenger, Grilly (FR); Pascal Valax, Chernex (CH); Gianni Baer, La Tour-de-Peilz (CH); Henri Kornmann, Versoix (CH)

(73) Assignee: Ares Trading S.A., Aubonne (CH)

( * ) Notice: Subject to any disclaimer, the term of this patent is extended or adjusted under 35 U.S.C. 154(b) by 445 days.

(21) Appl. No.: 11/916,087

(22) PCT Filed: Jun. 8, 2006

(86) PCT No.: PCT/EP2006/063029
§ 371 (c)(1),
(2), (4) Date: Nov. 30, 2007

(87) PCT Pub. No.: WO2006/131550
PCT Pub. Date: Dec. 14, 2006

(65) Prior Publication Data
US 2008/0200658 A1   Aug. 21, 2008

Related U.S. Application Data

(60) Provisional application No. 60/690,414, filed on Jun. 14, 2005.

(30) Foreign Application Priority Data

Jun. 10, 2005   (EP) .................................... 05105124

(51) Int. Cl.
*C07K 14/435*   (2006.01)
*C07D 251/02*   (2006.01)
(52) U.S. Cl. ......................... 530/413; 530/350; 544/216
(58) Field of Classification Search ........................ None
See application file for complete search history.

(56) References Cited

U.S. PATENT DOCUMENTS

| | | | |
|---|---|---|---|
| 4,588,585 A | 5/1986 | Mark et al. | |
| 4,737,462 A | 4/1988 | Mark et al. | |
| 4,879,111 A | 11/1989 | Chong | |
| 4,904,584 A | 2/1990 | Shaw | |
| 4,959,314 A | 9/1990 | Mark et al. | |
| 4,965,195 A | 10/1990 | Namen et al. | |
| 5,017,691 A | 5/1991 | Lee et al. | |
| 5,116,943 A | 5/1992 | Koths et al. | |
| 6,117,996 A * | 9/2000 | Lowe et al. | 544/216 |
| 6,605,280 B1 | 8/2003 | Novick et al. | |
| 6,773,599 B1 * | 8/2004 | Lowe et al. | 210/635 |
| 7,220,717 B2 * | 5/2007 | Novick et al. | 514/2 |
| 2007/0037734 A1 | 2/2007 | Rossi et al. | |
| 2007/0134761 A1 | 6/2007 | Chatellard et al. | |
| 2007/0196895 A1 | 8/2007 | Aloni et al. | |
| 2007/0258962 A1 | 11/2007 | Chatellard et al. | |
| 2007/0293658 A1 | 12/2007 | Kornmann et al. | |
| 2008/0076708 A1 | 3/2008 | Altarocca et al. | |
| 2008/0207876 A1 * | 8/2008 | Betley et al. | 530/344 |

FOREIGN PATENT DOCUMENTS

| | | |
|---|---|---|
| WO | WO 92/13095 | 8/1992 |
| WO | WO 99/09063 | 2/1999 |
| WO | WO 01/03737 | 1/2001 |
| WO | WO 01/07480 | 2/2001 |
| WO | WO 01/62285 | 8/2001 |
| WO | WO 01/85201 | 11/2001 |
| WO | WO 02/060479 | 8/2002 |
| WO | WO 02/092008 | 11/2002 |
| WO | WO 02/096456 | 12/2002 |
| WO | WO 02/101049 | 12/2002 |
| WO | WO 03/013577 | 2/2003 |
| WO | WO 03/080104 | 10/2003 |
| WO | WO 2004/081167 A2 | 9/2004 |
| WO | WO 2004/101617 A1 | 11/2004 |
| WO | WO 2005/040384 A1 | 5/2005 |
| WO | WO 2005/049649 A1 | 6/2005 |
| WO | WO 2005/083058 A1 | 9/2005 |
| WO | WO 2006/003134 A1 | 1/2006 |
| WO | WO 2006/128908 A1 | 12/2006 |
| WO | WO 2006/131768 A2 * | 12/2006 |

OTHER PUBLICATIONS

Altschul, S. F. et al. "Basic Local Alignment Search Tool" *Journal of Molecular Biology*, 1990, pp. 403-410, vol. 215.
Altschul, S. F. et al. "Gapped BLAST and PSI-BLAST a new generation of protein database search programs" *Nucleic Acids Research*, 1997, pp. 3389-3402, vol. 25, No. 17.
Devereux, J. et al. "A comprehensive set of sequence analysis programs for the VAX" *Nucleic Acids Research*, 1984, pp. 387-395, vol. 12, No. 1.
Grantham, R. "Amino Acid Difference Formula to Help Explain Protein Evolution" *Science*, Sep. 6, 1974, pp. 862-864, vol. 185, No. 4154.
Kim, S.-H. et al. "Structural requirements of six naturally occurring isoforms of the IL-18 binding protein to inhibit IL-18" *PNAS*, Feb. 1, 2000, pp. 1190-1195, vol. 97, No. 3.
Novick, D. et al. "Interleukin-18 Binding Protein: A Novel Modulator of the Th1 Cytokine Response" *Immunity*, Jan. 1999, pp. 127-136, vol. 10.
Pearson, W. R. "Rapid and Sensitive Sequence Comparison with FASTP and FASTA" *Methods in Enzymology*, 1990, pp. 63-98, vol. 183.
Puren, A. J. et al. "Gene expression, synthesis, and secretion of interleukin 18 and interleukin 1β are differentially regulated in human blood mononuclear cells and mouse spleen cells" *PNAS*, Mar. 1999, pp. 2256-2261, vol. 96.
Urushihara, N. et al. "Elevation of Serum Interleukin-18 Levels and Activation of Kupffer Cells in Biliary Atresia" *Journal of Pediatric Surgery*, Mar. 2000, pp. 446-449, vol. 35, No. 3.
Vigers, G. P. A. et al. "Crystal structure of the type-I interleukin-1 receptor complexed with interleukin-1β" *Nature*, Mar. 13, 1997, pp. 190-194, vol. 386.

* cited by examiner

*Primary Examiner* — Marianne P Allen
(74) *Attorney, Agent, or Firm* — Saliwanchik, Lloyd & Eisenschenk

(57) ABSTRACT

The invention relates to a process for the production of purified IL-18 binding protein (IL-18BP) from a fluid comprising affinity chromatography.

15 Claims, 3 Drawing Sheets

| Adsorbent | Fraction | Prot tot [μg/ml] | Vol [ml] | Tot Prot [μg] | IL18BP [μg/ml] | IL18BP tot [μg] | % Purity | %Recovery | % aggregates | % dimers | %monomers |
|---|---|---|---|---|---|---|---|---|---|---|---|
| Ligand #2 | Load | 602 | 80 | 48160 | 216.4 | 17312 | 36 | 100 | 6.92 | 22.39 | 70.67 |
| | NB | 124 | 118 | 14632 | 37.7 | 4448.6 | 30 | 26 | 0 | 6.74 | 93.26 |
| | E | 727 | 10 | 7270 | 834.6 | 8346 | 115 | 48 | 0.25 | 13.53 | 86.22 |
| | ET | 257 | 5 | 1285 | 272 | 1360 | 106 | 8 | 0.66 | 17.02 | 82.32 |
| Ligand #5 | Load | 646 | 80 | 51680 | 229.1 | 18328 | 35 | 100 | 7.64 | 22.37 | 69.99 |
| | NB | 91 | 100 | 9100 | n.d. | n.d. | n.d. | n.d. | 0 | 3.55 | 96.45 |
| | E | 1279 | 10 | 12790 | 1153.1 | 11531 | 90 | 63 | 2.6 | 17.91 | 79.49 |
| | ET | 349 | 5 | 1745 | 376 | 1880 | 108 | 10 | 3.26 | 21.81 | 74.93 |
| Ligand #6 | Load | 577 | 80 | 46160 | 227.1 | 18168 | 39 | 100 | 5.6 | 23.3 | 71.1 |
| | NB | 48 | 116 | 5568 | n.d. | n.d. | n.d. | n.d. | 0 | 3.85 | 96.15 |
| | E | 887 | 10 | 8870 | 1026.1 | 10261 | 116 | 56 | 0 | 10.91 | 89.09 |
| | ET | 365 | 5 | 1825 | 428.7 | 2143.5 | 117 | 12 | 0 | 8.96 | 91.04 |
| Ligand #7 | Load | 701 | 80 | 56080 | 221.3 | 17704 | 32 | 100 | 4.4 | 23.91 | 71.65 |
| | NB | 54 | 110 | 5940 | 9.9 | 1089 | 18 | 6 | 0 | 4.82 | 95.18 |
| | E | 867 | 10 | 8670 | 803 | 8030 | 93 | 45 | 0 | 10.84 | 89.16 |
| | ET | 247 | 5 | 1235 | 346.8 | 1734 | 140 | 10 | 0 | 12.69 | 87.31 |

Figure 2

| Expt | Wash Conditions (Recovery/Monomer/Dimer %/%/%) | Elution Conditions (All at pH 7.0 unless stated) (Recovery/Monomer/Dimer (%/%/%)) | NB (%) | Overall Recovery (%) |
|---|---|---|---|---|
| 1 | None | PBS/50% EG/500 mM NaCl (75/88/12) | 1.7 | 76.7 |
| 2 | PBS, pH 7.0 (10/84/16) | PBS/10% EG (3.7/96/4)<br>PBS/20% EG (5.4/90/10)<br>PBS/30% EG (9.6/92/8)<br>PBS/40% EG (7.9/80/20)<br>PBS/50% EG/500 Mm NaCl (2.4/n.d./n.d.) | 0 | 51.8 |
| 3 | PBS, pH 7.0 (10/84/16) | PBS/0.5 M NaCl (0.2/ n.d./n.d)<br>PBS/1.0 M NaCl (0/ n.d./n.d)<br>PBS/1.5 N NaCl (0/ n.d./n.d)<br>PBS/2.0 M NaCl (0/ n.d./n.d)<br>PBS/50% EG/500 mM NaCl (46.7/91/9) | 0 | 56.9 |
| 4 | PBS, pH 7.0 (14.8/ n.d/n.d) | PBS/2 M Ammonium thiocyanate (35.6/ n.d./n.d)<br>PBS/50% EG/500 mM NaCl (8.4/ n.d./n.d) | 3.1 | 58.8 |
| 5 | None | PBS/1% PEG pH 7.0 (15.1/ n.d./n.d)<br>PBS/1% PEG pH 8.5 (2.9/ n.d./n.d)<br>PBS/50% EG/500 mM NaCl (42.3/ n.d./n.d) | 0 | 60.3 |

Figure 3

PROCESS FOR THE PURIFICATION OF IL-18 BINDING PROTEIN

Cross-Reference to Related Application

This application is the U.S. national stage application of International Patent Application No. PCT/EP2006/063029, filed Jun. 8, 2006, which claims the benefit of U.S. Provisional Patent Application Ser. No. 60/690,414, filed Jun. 14, 2005, the disclosures of which are hereby incorporated by reference in their entireties, including all figures, tables and amino acid or nucleic acid sequences.

FIELD OF THE INVENTION

The present invention is in the field of protein purification. More specifically, it relates to the purification of IL-18 binding protein (IL-18BP) via affinity chromatography. Specifically, the invention comprises the use of a synthetic ligand in affinity chromatography.

BACKGROUND OF THE INVENTION

Proteins have become commercially important as drugs that are also generally called "biologicals". One of the greatest challenges is the development of cost effective and efficient processes for purification of proteins on a commercial scale. Many methods are now available for large-scale preparation of proteins. However, crude products, contain also complex mixtures of impurities, which are sometimes difficult to separate from the desired product.

The health authorities request high standards of purity for proteins intended for human administration. In addition, many purification methods may contain steps requiring application of low or high pH, high salt concentrations or other extreme conditions that may jeopardize the biological activity of a given protein. Thus, for any protein it is a challenge to establish a purification process allowing for sufficient purity while retaining the biological activity of the protein.

Chromatography is an appropriate purification technology because it allows the separation of molecules having similar physico-chemical properties. Of the different type of chromatography, ion exchange chromatography, hydrophobic interaction chromatography, reverse phase chromatography and affinity chromatography are the most commonly used for industrial processes.

Ion exchange chromatographic systems have been used widely for separation of proteins primarily on the basis of differences in charge. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

Anion exchangers can be classified as either weak or strong. The charge group on a weak anion exchanger is a weak base, which becomes de-protonated and, therefore, looses its charge at high pH. DEAE-cellulose is an example of a weak anion exchanger, where the amino group can be positively charged below pH ~9 and gradually loses its charge at higher pH values. Diethylaminoethyl (DEAE) or diethyl-(2-hydroxy-propyl)aminoethyl (QAE) have chloride as counter ion, for instance.

A strong anion exchanger, on the other hand, contains a strong base, which remains positively charged throughout the pH range normally used for ion exchange chromatography (pH 1-14). Q-sepharose (Q stands for quaternary ammonium) is an example for a strong anion exchanger.

Cation exchangers can also be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Carboxymethyl (CM) and sulfopropyl (SP) have sodium as counter ion, for example.

Chromatographic systems having a hydrophobic stationary phase have also been widely employed in the purification of proteins. Included in this category are hydrophobic interaction chromatography (HIC) and reversed phase liquid chromatography (RPLC). The physicochemical basis for separation by HIC and RPLC is the hydrophobic effect, proteins are separated on a hydrophobic stationary phase based on differences in hydrophobicity.

In HIC, generally, sample molecules in a high salt buffer are loaded on the HIC column. The salt in the buffer interacts with water molecules to reduce the solvation of the molecules in solution, thereby exposing hydrophobic regions in the sample molecules, which are consequently adsorbed by the HIC column. The more hydrophobic the molecule, the less salt needed to promote binding. Usually, a decreasing salt gradient is used to elute samples from the column. As the ionic strength decreases, the exposure of the hydrophilic regions of the molecules increases and molecules elute from the column in order of increasing hydrophobicity. Sample elution may also be achieved by the addition of mild organic modifiers or detergents to the elution buffer. HIC is reviewed e.g. in Protein Purification, 2d Ed., Springer-Verlag, New York, pgs 176-179 (1988).

In HIC, different chromatographic supports are available carrying various ligands. The ligands differ with respect to their hydrophobicity. Commonly used hydrophobic ligands are phenyl-, butyl- or octyl-residues.

Reverse phase chromatography is a protein purification method closely related to HIC, as both are based upon interactions between solvent-accessible non-polar groups on the surface of biomolecules and hydrophobic ligands of the matrix. However, ligands used in reverse phase chromatography are more highly substituted with hydrophobic ligands than HIC ligands. While the degree of substitution of HIC adsorbents may be in the range of 10-50 µmoles/mL of matrix of C2-C8 aryl ligands, several hundred µmoles/mL of matrix of C4-C8 alkyl ligands are usually used for reverse phase chromatography adsorbents.

Hydrophobic interaction chromatography and reverse phase chromatography are also distinct in that hydrophobic interaction chromatography is performed in aqueous solvent conditions and changes in ionic strength are used to elute the column. The protein typically binds in the native state via hydrophobic groups located on the surface of the protein, and the native state is retained during the elution conditions. In contrast to this, reverse phase chromatography utilizes a hydrophobic solvent (typically acetonitrile) and the binding of a ligand is a function of the phase partition between the hydrophobic nature of the solvent and column functional group. Proteins are typically denatured to some extent in such solvents and bind due to the hydrophobic nature of the entire polypeptide sequence. Since the majority of hydrophobic groups are located in the core of globular proteins, the binding is related to the extent of denaturation of the protein and the accessibility of these groups to the column functional groups.

Among the different techniques for protein purification, affinity chromatography deserves particular attention. It satisfies the requirement for ultra-high selectivity of the target protein from complex mixtures of impurities, thereby providing a better product quality.

Affinity chromatography relies on the biological functions of a protein to bind a ligand, i.e. a specific component, such as metal ions, peptides, chemical molecules, proteins, nucleic acids that is attached to a column matrix. This ligand can be immobilized or attached to a variety of matrixes, such as cellulose or agarose. The target protein is then passed through the column and bound to it via the ligand, while other proteins elute out. Purification of a target protein is usually achieved by passing a solution containing the target protein through the column that exhibits a high amount of attached or immobilized ligands. This is a very efficient purification method since it relies on the biological specificity of the target protein, such as the affinity of an enzyme for a substrate.

However, the variety of ligand available that can be attached to a matrix is enormous and the selection of the optimal ligand can not be easily inferred from one protein to the other. At least three limiting factors come into play, namely the different affinity of proteins to certain ligands, the immobilization of the ligand to the matrix in a sufficiently high amount and the potentially restricted accessibility of the ligand to the binding sites of the protein. Thus, it is extremely difficult to state a priori, which affinity chromatrography matrix will bind the target protein.

Interleukin-18 binding protein (IL-18BP) is a naturally occurring soluble protein that was initially affinity purified, on an IL-18 column, from urine (Novick et al. 1999). IL-18BP abolishes IL-18 induction of IFN-γ and IL-18 activation of NF-κB in vitro. In addition, IL-18BP inhibits induction of IFN-γ in mice injected with LPS.

The IL-18BP gene was localized to the human chromosome 11, and no exon coding for a transmembrane domain could be found in the 8.3 kb genomic sequence comprising the IL-18BP gene. Four isoforms of IL-18BP generated by alternative mRNA splicing have been identified in humans so far. They were designated IL-18BP a, b, c, and d, all sharing the same N-terminus and differing in the C-terminus (Novick et al 1999). These isoforms vary in their ability to bind IL-18 (Kim et al. 2000). Of the four human IL-18BP (hIL-18BP) isoforms, isoforms a and c are known to have a neutralizing capacity for IL-18. The most abundant IL-18BP isoform, isoform a, exhibits a high affinity for IL-18 with a rapid on-rate and a slow off-rate, and a dissociation constant (Kd) of approximately 0.4 nM (Kim et al. 2000). IL-18BP is constitutively expressed in the spleen, and belongs to the immunoglobulin superfamily. The residues involved in the interaction of IL-18 with IL-18BP have been described through the use of computer modelling (Kim et al. 2000) and based on the interaction between the similar protein IL-1 with the IL-1R type I (Vigers et al. 1997).

IL-18BP is constitutively present in many cells (Puren et al. 1999) and circulates in healthy humans (Urushihara et al. 2000), representing a unique phenomenon in cytokine biology. Due to the high affinity of IL-18BP to IL-18 (Kd=0.4 nM) as well as the high concentration of IL-18BP found in the circulation (20 fold molar excess over IL-18), it has been speculated that most, if not all of the IL-18 molecules in the circulation are bound to IL-18BP. Thus, the circulating IL-18BP that competes with cell surface receptors for IL-18 may act as a natural anti-inflammatory and an immunosuppressive molecule.

IL-18BP has been suggested as a therapeutic protein in a number of diseases and disorders, such as psoriasis, Crohn's Disease, rheumatoid arthritis, psoriatic arthritis, liver injury, sepsis, atherosclerosis, ischemic heart diseases, allergies, etc., see e.g. WO 99/09063, WO 01/07480, WO 01/62285, WO 01/85201, WO 02/060479, WO 02/096456, WO 03/080104, WO 02/092008, WO 02/101049, WO 03/013577. Given that IL-18BP is suggested as a therapeutic protein for administration e.g. to humans, there is an unmet need for adequate amounts of IL-18BP in sufficiently high purity.

A purification process for IL-18BP has been described in WO 2005/049649. However, this process does not comprise a step of affinity chromatography.

Thus, an alternative purification process resulting in IL-18BP in good purity and in high yield is desirable.

SUMMARY OF THE INVENTION

The present invention is based on the development of a purification process for proteins, in particular IL-18 binding protein (IL-18BP).

Therefore, in a first aspect, the invention relates to the use of synthetic affinity chromatography ligands according to formula (I)

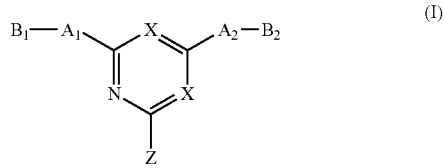

wherein $A_1$, $A_2$, $B_1$, $B_2$, X and Z are defined as described in the detailed description below, for the production of purified IL-18BP.

In a second aspect, the invention relates to a process for the production of purified IL-18 binding protein (IL-18BP) from a fluid comprising an affinity chromatography step utilizing a synthetic ligand according to formula (I), which is attached to a matrix.

BRIEF DESCRIPTION OF THE DRAWINGS

FIG. 2 Shows recoveries and purities of fractions from affinity chromatography runs with affinity ligand #2, #5, #6 and #7. NB=non-bound fraction, E=eluate, ET=elution tail.

FIG. 3 Shows the influence of different washing and elution buffers on the yields for total recovered IL-18BP protein, its monomeric form and its dimeric form. The purification was carried out with affinity ligand #6. EG=ethylene glycol, PEG=propylene glycol, NB=non-bound fraction; n.d.=not determined. The value for "Recovery" is calculated as follows: (IL18BP (g) in the elution fraction)/(total IL18BP (g) loaded on the column).

DETAILED DESCRIPTION OF THE INVENTION

Figure 1:
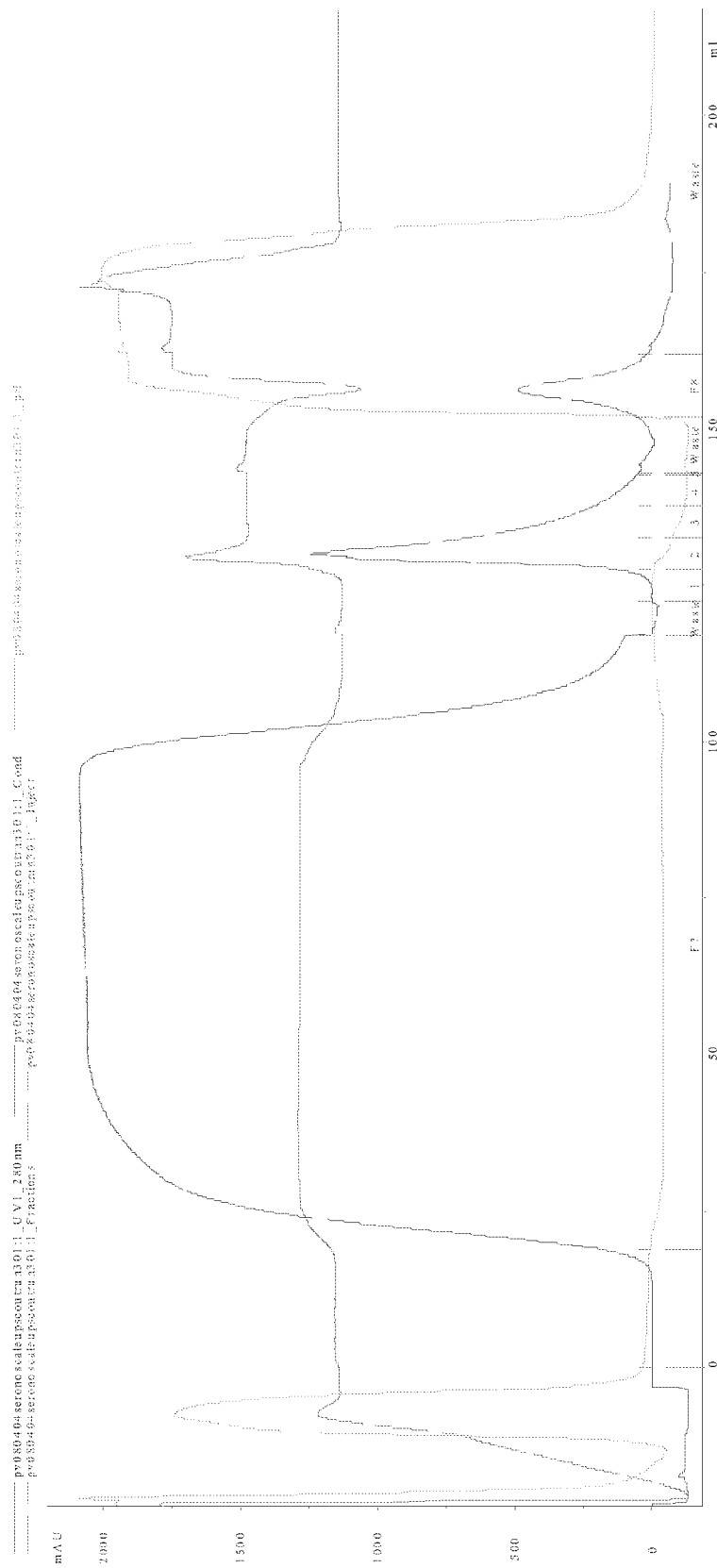
FIG. 1 Shows a typical elution profile using affinity ligand #5. F7—non-bound; 2,3—elution; 4—elution tail; F8—strip.

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like. The aryl ring may be also fused to a heterocycloalkyl group. Such fused aryls include dihydrobenzimidazole-2-one, benzo[1,3]dioxole and the like.

"$C_1$-$C_6$-alkyl aryl" refers to $C_1$-$C_6$-alkyl groups having an aryl substituent, such as, for example, benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,3,5-triazolyl, 1,2,3-oxadiazolyl, 1,2,4-oxadiazolyl, 1,2,5-oxadiazolyl, 1,2,3-triazinyl, 1,3,5-triazinyl, 1,3,4-thiadiazolyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnnolinyl, napthyridinyl, pyridazinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"$C_2$-$C_6$-alkenyl" refers to alkenyl groups preferably having from 2 to 6 carbon atoms and having one or more sites of alkenyl unsaturation. Preferred alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having one or more sites of alkynyl unsaturation. Preferred alkynyl groups include ethynyl (—C≡CH), propynyl (—$CH_2$C≡CH), and the like.

"Acyl" refers to the group —C(O)R where R includes "$C_1$-$C_6$-alkyl", "aryl", "heteroaryl", "$C_3$-$C_8$-cycloalkyl", "$C_3$-$C_8$-heterocycloalkyl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g a —S—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"Amine" refers to a group with the structure —NRR', wherein R and R' includes hydrogen, or "$C_1$-$C_6$-alkyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Ether" refers to a group with the structure —O—.

"Thioether" refers to a group with the structure —S—.

"Substituted or unsubstituted", unless otherwise constrained by the definition of the individual substituent, the above set out groups, like "alkyl", "alkenyl", "alkynyl", "alkoxy", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quaternary ammonium moieties, "acyl", "acyloxy", "acylamino", "aminocarbonyl", "alkoxycarbonyl", "aryl", "aryloxy", "heteroaryl", "heteroaryloxy", carboxyl, cyano, halogen, hydroxy, sulfanyl, nitro, sulphoxy, sulphonyl, sulphonamide, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, animals formed by ring closure for instance in an effort to obtain a protective group.

The present invention is based on the development of a purification process for IL-18BP resulting in purified IL-18BP.

In a first aspect the invention relates to the use of a synthetic affinity chromatography ligand according to formula (I)

$$B_1-A_1 \diagdown X \diagdown A_2-B_2 \atop N \diagdown X \atop Z \quad (I)$$

wherein $A_1$ and $A_2$ are selected from the group consisting of an amine, ether and thioether of the structures:

$$Y \leftarrow \underset{\underset{R_1}{|}}{N} \rightarrow B \qquad Y \leftarrow O \rightarrow B \qquad Y \leftarrow S \rightarrow B$$

wherein $R_1$ is selected from the group consisting of hydrogen, a substituted or unsubstituted $C_1$-$C_6$—alkyl, substituted or unsubstituted aryl and substituted or unsubstituted $C_1$-$C_6$—alkyl aryl;

$B_1$ and $B_2$ are independently selected from the group consisting of substituted or unsubstituted $C_1$-$C_6$-alkyl, substituted or unsubstituted $C_3$-$C_8$-cycloalkyl and substituted or unsubstituted aryl, wherein said $B_1$ and $B_2$ are independently optionally substituted with $R_2$, $OR_2$, $SR_2$, or $N(R_2)_2$; wherein each $R_2$ is independently selected from the group of hydrogen, substituted or unsubstituted $C_1$-$C_6$-alkyl, substituted or unsubstituted aryl and substituted or unsubstituted $C_1$-$C_6$-alkyl aryl;

each X represents independently a nitrogen, a carbon carrying a hydrogen, a carbon carrying a chlorine group or a carbon carrying a cyano group; and Z is a functional group capable of reaction with a matrix, for the production of purified IL-18 binding protein (IL-18BP).

In a further embodiment, the affinity chromatography ligand according to formula (I) can be used to the production of purified proteins.

The term "matrix", as used herein, relates to any matrix or carrier material used in chromatography, such as polysaccharide-based matrixes (e.g. agarose, sepharose, dextran, sephadex), synthetic-based matrixes (e.g. methacrylate, polystyrene, divinylbenzene) or mineral-based matrixes (e.g. ceramic, silica). The matrix materials may be present in different cross-linked forms, depending on the specific material. The material may be used as beads. The volume of the resin, as well as the length and diameter of column to be used depends on several parameters such as the volume of fluid to be treated, concentration of protein in the fluid to be subjected to the process of the invention, etc., and determining this is well within the skills of the person skilled in the art.

The functional group Z may be any group capable for forming a bond between the ligand and the matrix, such as e.g. amine, azide, hydroxyl or the like. Z can also be a functional group attached to the matrix, such as e.g. an amine of amine-activated agarose that reacts directly with the ligand. The functional group can also introduce a spacer to improve binding capacity or selectivity for the target protein. Spacer lengths of $C_1$-$C_8$ (i.e. 1-8 carbon atoms) can be introduced by easy chemical reactions well known to the person skilled in the art.

In a preferred embodiment the invention relates to the use of a synthetic affinity chromatography ligand according to formula (II)

$$B_1-A_1 \diagdown N \diagdown A_2-B_2 \atop N \diagdown N \atop Z \quad (II)$$

wherein $A_1$, $A_2$, $B_1$, $B_2$ and Z are defined as above, for the production of purified IL-18 binding protein (IL-18BP).

In another embodiment, $A_1$ and $A_2$ are an amine.

In another embodiment, $B_1$ and $B_2$ are independently selected from the group consisting of $C_1$-$C_6$-alkyl, $C_3$-$C_8$-cycloalkyl and aryl; wherein said $B_1$ and $B_2$ are independently optionally substituted with $R_2$, $OR_2$, $SR_2$, or $N(R_2)_2$; and each $R_2$ is independently selected from the group consisting of hydrogen, $C_1$-$C_6$-alkyl, aryl and $C_1$-$C_6$-alkyl aryl.

In a preferred embodiment $B_1$ and $B_2$ or said substituted $B_1$ and $B_2$ are independently selected from the group of:

wherein "*" refers to the position where B is connected to A.

In one embodiment $B_1$ and $B_2$ are identical.

In a preferred embodiment, $B_1$ and $B_2$ are n-hexyl.

In a further preferred embodiment, $A_1$ and $A_2$ are an amine, with the structure —$N(CH_3)$—.

In a preferred embodiment each X is nitrogen.

In a further preferred embodiment Z is NH.

There are several potential routes for the immobilization of the ligand to the matrix. One potential route starting with the reaction of trichlorotriazine with an amine is depicted in Scheme 1:

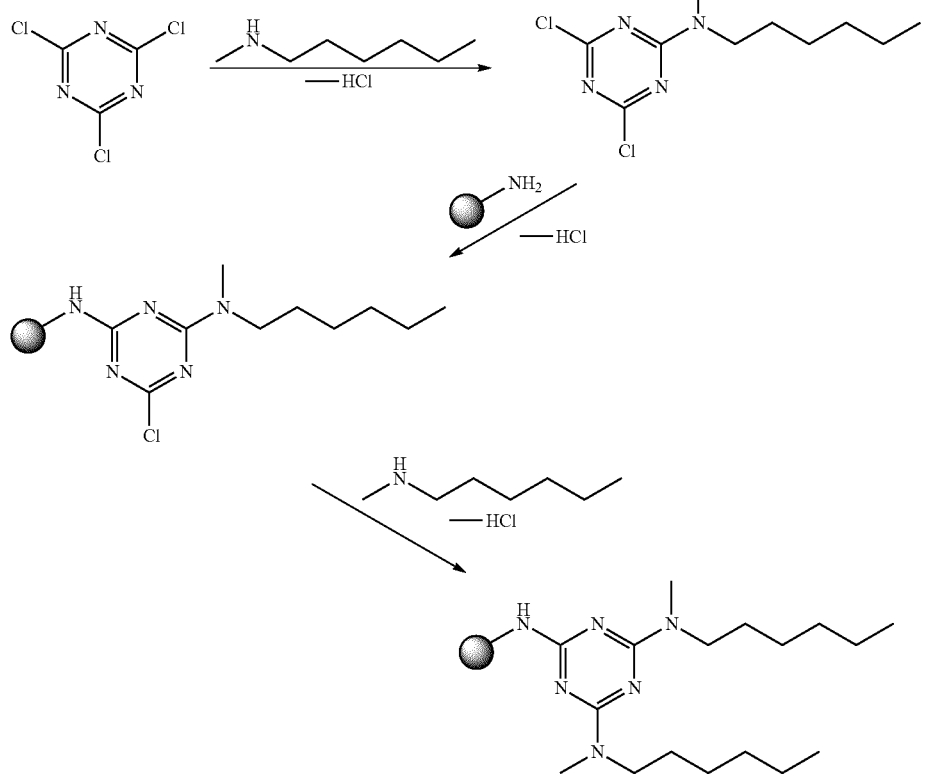

Another route starts with the attachment of the trichlorotriazine to the amine-activated matrix, followed by reaction with the amine. A third route would be the attachment of two amines to trichlorotriazine followed by the attachment of the substituted chlorotriazine to an amine-activated matrix. These general routes can be applied to a variety of protocols known to the person skilled in the art.

The amine-activated matrix can be prepared by amination of any commercial matrix material or can be purchased from commercial sources. Spacers of different length can be inserted between the matrix and the functional group or the functional group and the ligand by reaction of bifunctional reagents like ethylendiamine, propylenediamine or the like with the matrix material, or the ligand or by introducing spacers.

In a preferred embodiment the functional group is directly attached to the matrix without any spacer.

In one embodiment the affinity ligand density of the column is between 5 μmol/g-55 μmol/g.

In another embodiment, the affinity ligand density is 10, 20, 30, 40 or 50 μmol/g.

In a preferred embodiment the affinity ligand density is 20 μmol/g of resin.

In a preferred embodiment the affinity ligand as defined above is used for production of purified human, recombinant IL-18BP.

In another preferred embodiment, the affinity ligand is used for production of IL-18BP from serum-free cell culture supernatant.

In another embodiment, the affinity ligand is used for the capture of IL-18BP from a fluid.

In a second aspect, the invention relates to a process for the production of purified proteins, specifically IL-18 binding protein (IL-18BP) comprising subjecting a fluid to affinity chromatography, which utilizes the affinity ligand as described above.

In one embodiment, the process is carried out at temperature between 4-37° C.

In a preferred embodiment, the process is carried out at room temperature (16-25° C.).

In one embodiment, the process recovers more than 40% or more than 50% pure IL-18BP after affinity chromatography.

In a preferred embodiment, the process yields pure IL-18BP of >60% or >70% or >80% after the affinity chromatography.

In a preferred embodiment, the process yields pure IL-18BP, wherein the percentage of monomer IL-18BP is higher than 80%. Wherein, pure relates to a purity of higher than 95% as determined by Bradford analysis or less than 100.000 ppm host cell proteins (HCP) measured by ELISA.

In another preferred embodiment, the percentage of monomer IL-18BP is at least 95% or even higher than 95% after the affinity chromatography step.

In one embodiment, the process further comprises one or more additional chromatography steps selected from the group consisting of hydrophobic charge induction chromatography (e.g. 4-mercaptoethyl-pyridine (MEP) as immobilized ligand), immobilized metal ion affinity chromatography (e.g. on a chelating sepharose), ion exchange chromatography (e.g. a carboxymethyl (CM)-resin, such as CM sepharose FF), hydrophobic interaction chromatography (e.g. on a phenyl resin, such as phenyl sepharose FF), and reverse phase chromatography, e.g. on a reverse phase-source 30 RPC. It is particularly preferred to use purification step comprising the affinity ligand of the invention in combination with any one of the above-mentioned chromatography steps or in any combination with each other. Preferably, the affinity chromatography is used for capture of IL-18PB from a fluid such as e.g. cell culture harvest.

More preferably, the affinity chromatography is followed by the following further purifications steps:

(a) Subjecting the eluate of the affinity chromatography to immobilized metal ion affinity chromatography;

(b) Subjecting the eluate of the metal ion affinity chromatography to hydrophobic charge-interaction chromatography;

(c) Subjecting the eluate of the hydrophobic charge-interaction chromatography to cation exchange chromatography;

(d) Subjecting the flow-through of the cation exchange chromatography to hydrophobic interaction chromatography;

(e) Subjecting the eluate of the hydrophobic interaction chromatography to reverse phase chromatography.

Step (a) is preferably carried out on a chelating sepharose column, such as a chelating sepharose fast flow column, having $Zn^{2+}$ ions chelated. Preferably, binding of IL-18BP is carried out at pH 8.5±0.1, preferably in 50 mM sodium phosphate and 0.5 M NaCl having this pH. A washing step may be carried out with 15 mM ammonium chloride in equilibration buffer. Elution is preferably carried out at pH 9.0±0.5, e.g. at pH 8.7 or at pH 9, e.g. in 0.075 M ammonium acetate or in 0.06 M ammonium acetate having this pH.

Step (b) is preferably carried out on a MEP (4-mercaptoethylpyridine derivative) column, such as MEP HyperCel® (LifeSciences). Binding of IL-18BP is carried out preferably at pH 6.1±0.1, e.g. in PBS 1X+1 NaCl having this pH. Elution is carried out preferably at pH 8.4±0.1, e.g. in with 20 mM phosphate buffer plus 35% propylene glycol, the mixture having pH 8.4±0.1.

Step (c) is preferably carried out on a carboxymethylsepharose (CM) column. This is a step in which the flow-through is collected for further purification. This step is based on the fact that under specific circumstances relating e.g. to salt and pH conditions, IL-18BP does not bind to the resin, while impurities (e.g. host cell proteins, serum-derived proteins) that is used for bind to it. Preferably, step (c) is carried out at pH 6.0±0.2, for example in the presence of 1 mM MES (N-morpholinoethanesulfonic acid).

Step (d) is preferably carried out on a phenyl sepharose column, such as a Phenyl-Sepahrose Fast Flow column. Preferably, binding of IL-18BP is carried out at about pH 9.1±0.2, e.g. in 50 mM sodium borate and 0.9 M ammonium sulphate or 0.10 M ammonium sulfate having this pH. The elution from the phenyl-sepharose column is preferably carried out at pH 9.1±0.2 in the presence of an elevated salt concentration, such as in 50 mM sodium borate 9.1±0.2, 0.15M ammonium sulphate having this pH.

Step (e) is preferably carried out on a Source 30 RPC column. Binding of IL-18BP to the column material is preferably carried out at pH 9.1±0.2, e.g. in 50 mM sodium borate buffer. Elution is preferably carried out using a gradient, IL-18BP eluting around 28-32% of 0.1% trifluoroacetic acid (TFA) in acetonitrile.

It is understood that the conditions described above in connection with steps (a) to (e) of the purification may also be applied when carrying out single steps of the invention, or (sub-)combinations of steps.

In another embodiment, the process further comprises one or more virus removal filtration steps.

In another embodiment, the process for the production of purified IL-18BP of IL-18BP produces human, recombinant IL-18BP.

In another embodiment, the process starts with a fluid, wherein the fluid is serum-free cell culture supernatant.

Several parameters of the purification process can be varied to improve binding capacity of the affinity column and selectivity of the purification of IL-18BP (e.g. temperature, pH, salt concentration of equilibration buffer, loading buffer and/or elution buffer).

In one embodiment, the equilibration buffer PBS pH 7.0.

In another embodiment, the equilibration buffer is sodium phosphate buffer with a pH between 5.5-7.0.

In another embodiment, the sodium phosphate equilibration buffer additionally comprises $Na_2SO_4$.

In one embodiment, the affinity column is charged with a fluid comprising IL-18BP, whereby the fluid is applied onto the column in a mixture of sodium phosphate and sodium sulfate buffer with a pH between 5.5-7.0.

In a preferred embodiment the pH of the loading buffer is 5.5.

In one embodiment, the buffer further comprises $Na_2SO_4$, to further enhance the binding capacity.

In another embodiment, the fluid comprises clarified bioreactor harvest.

In one embodiment, the affinity column is washed with buffer selected from the group of sodium phosphate, sodium sulfate and PBS at pH 7.0, to remove unspecifically bound proteins after charging the fluid comprising IL-18BP to affinity column.

In another embodiment the washing buffer further comprises $Na_2SO_4$.

In one embodiment, the elution of IL-18BP is carried out in a buffer comprising a mixture of sodium phosphate buffer and propylene glycol at pH 7.

In another embodiment the percentage of propylene glycol in the elution buffer mixture is between 5%-70%.

In another embodiment, the percentage of propylene glycol is between 30%-50%.

In a preferred embodiment, the elution buffer comprises a mixture of 50 mM sodium phosphate and 35% propylene glycol at pH 7.

In another embodiment, the elution buffer comprises PBS.

In another embodiment, the PBS elution buffer additionally comprises 10%, 20%, 30%, 40%, 50% or 60% ethylene glycol.

In another embodiment, the PBS elution buffer additionally comprises 10%, 20%, 30%, 40%, 50% or 60% propylene glycol.

In another embodiment, the PBS elution buffer additionally comprises 0.5M, 1.0M, 1.5M or 2.0M sodium chloride.

In another embodiment, the elution buffer comprises additionally sodium chloride and ethylene glycol or propylene glycol.

In one embodiment, the cell fluid may be centrifuged or filtrated before loading the cell fluid onto the column.

In another preferred embodiment the fluid comprising IL-18BP is filtered through a 0.45 μm filter before charging the fluid to the affinity column.

In another embodiment, the process of the invention further comprises one or more additional chromatography step selected from the group consisting of hydrophobic interaction chromatography, reverse phase chromatography and anionic exchange chromatography.

In a preferred embodiment, the process of the invention further comprises
  a. hydrophobic interaction chromatography,
  b. reverse phase chromatography, and
  c. anionic exchange chromatography.

If the protein purified according to the process of the invention is intended for administration to humans, it is advantageous to further include one or more steps of virus removal in the process. Preferably, a virus removal filtration step is carried out after the affinity chromatography.

If the initial volume of fluid from which IL-18BP is purified is large, it may be advantageous to reduce the volume of material by capturing the protein and re-suspending it in a smaller volume of buffer before actually starting the purification process.

In order to facilitate storage or transport, for instance, the material may be frozen and thawed before and/or after any purification step of the invention.

In accordance with the present invention, IL-18BP to be purified may be native, i.e. naturally occurring IL-18BP. It may thus be purified from any natural source or material, such as e.g. from body fluids such as urine.

IL-18BP may also be derived from any animal or human source. Preferably, the IL-18BP to be purified is human, and more preferably it is recombinant IL-18BP. Recombinant IL-18BP may be produced in prokaryotic expression systems, such as in bacterial systems as *Escherichia coli*. It may also be produced in eukaryotic expression systems, such as yeast, insect, or mammalian cells. In accordance with the present invention, it is preferred to express IL-18BP in mammalian cells such as animal cell lines, or in human cell lines. Chinese hamster ovary cells (CHO) are an example of a cell line that is particularly suitable for expression of IL-18BP.

If IL-18BP to be purified is expressed by mammalian cells secreting it, the starting material of the purification process of the invention is cell culture supernatant, also called harvest or crude IL-18BP. If the cells are cultured in a medium containing animal serum, the cell culture supernatant also contains serum proteins as impurities.

Preferably, the IL-18BP expressing cells are cultured under serum-free conditions. In this case, the starting material of the purification process of the invention is serum-free cell culture supernatant that mainly contains host cell proteins as impurities. If growth factors are added to the cell culture medium, such as insulin, for example, these proteins will preferably be eliminated during the purification process as well.

Since IL-18BP is a soluble, secreted protein, it is released into the cell culture supernatant, either by means of its natural signal peptide, or by means of a heterologous signal peptide, i.e. a signal peptide derived from another secreted protein which may be more efficient in the particular expression system used. The fluid from which IL-18BP is purified is thus preferably cell culture supernatant, such as e.g. CHO-cell supernatant. Cell culture supernatant may comprise animal derived serum, if cells are cultured in serum containing medium. It is preferred to purify the protein from the supernatant of cells that were grown in serum-free medium, i.e. in culturing medium not containing serum derived from fetal calf or other animal sources.

The term "IL-18 binding protein" is used herein synonymously with "IL-18BP". This term relates IL-18 binding proteins such as the ones defined in WO 99/09063 or in Novick et al., 1999. The term IL-18BP includes splice variants and/or isoforms of IL-18 binding proteins, as the ones defined in Kim et al., 2000, in particular human isoforms a and c of IL-18BP. The term "IL-18PB", as used herein, further includes muteins, functional derivatives, active fractions, fused proteins, circularly permutated proteins and slats of IL-18BP as defined in WO 99/09063.

The IL-18BP subject to the purification process according to the present invention may be glycosylated or non-glycosylated, it may be derived from natural sources, such as urine, or it may preferably be produced recombinantly. Recombinant expression may be carried out in prokaryotic expression systems like *E. coli*, or in eukaryotic, and preferably in mammalian, expression systems.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP (both disclosed in WO99/09063) under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nim.nih.gov) and FASTA (Pearson W R, 1990).

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In a preferred embodiment, any such mutein has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |

TABLE I-continued

Preferred Groups of Synonymous Amino Acids

| Amino Acid | Synonymous Group |
|---|---|
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of IL-18 inhibitor molecule, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the IL-18 inhibitor, such as induction of IFN-gamma in blood cells.

The sequences of IL-18BP and its splice variants/isoforms can be taken from WO99/09063 or from Novick et al., 1999, as well as from Kim et al., 2000.

Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example. Therefore, in a preferred embodiment, the functional derivative comprises at least one moiety attached to one or more functional groups, which occur as one or more side chains on the amino acid residues. An embodiment in which the moiety is a polyethylene glycol (PEG) moiety is highly preferred.

In a further preferred embodiment of the invention, IL-18BP comprises an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, IL-18BP is fused to the constant region of an Ig molecule. Preferably, it is fused to heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

In a third aspect, the invention relates to a protein purified by the process of purification according to the invention. In the following, such protein is also called "purified IL-18BP". Such purified IL-18BP is preferably highly purified IL-18BP. Highly purified IL-18BP is determined e.g. by the presence of a single band in a silver-stained PAGE-gel after loading of protein in the amount of 2 mcg per lane. Purified IL-18BP may also be defined as moving as a single peak in HPLC. Purified IL-18BP may also be defined as moving as a single peak in HPLC.

The IL-18BP preparation obtained from the purification process of the invention may contain less than 20% of impurities, preferably less than 10%, 5%, 3%, 2% or 1% of impurities, or it may be purified to homogeneity, i.e. being free from any proteinaceous contaminants.

Purified IL-18BP may be intended for therapeutic use, i.e. for administration to patients. If purified IL-18BP is administered to patients, it is preferably administered systemically, and preferably subcutaneously or intramuscularly, or topically, i.e. locally. Rectal or intrathecal administration may also be suitable, depending on the specific use of purified IL-18BP.

For this purpose, purified IL-18BP may be formulated as a pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s)

may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity).

A "therapeutically effective amount" is such that when administered, the IL-18 inhibitor results in inhibition of the biological activity of IL-18. The dosage administered, as single or multiple doses, to an individual will vary depending upon a variety of factors, including IL-18 inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

Purified IL-18BP may be used in an amount of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

In further preferred embodiments, the purified IL-18BP is administered daily or every other day or three times per week or once per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, purified IL-18BP can be administered prophylactically or therapeutically to an individual prior to, simultaneously or sequentially with other therapeutic regimens or agents (e.g. multiple drug regimens), in a therapeutically effective amount.

Purified IL-18BP may be used for preparation of a medicament for treatment and/or prevention of a number of diseases or disorders. Such diseases or disorders are preferably IL-18 mediated disorders. In particular, purified IL-18BP may be used for treatment and/or prevention of psoriasis, psoriatic arthritis, Crohn's Disease, rheumatoid arthritis, liver injury such as alcoholic liver cirrhosis, sepsis, atherosclerosis, ischemic heart diseases, allergies, in particular delayed-type hypersensitivity, and closed head injury.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE 1

Purification of Recombinant, Human IL-18BP from Serum-Free Cho Cell Supernatant

Affinity columns, comprising immobilized affinity ligands according to formulae (I) or (II) were used for purification purposes.

The affinity ligand was attached to a matrix as outlined in synthetic scheme 1. The column was packed with the synthesized affinity column material following general instructions for commercial affinity chromatography material and once run blank before use.

1 ml fritted, gravity-fed Piksi Kit columns were equilibrated with 15 CV (column volumes) of PBS at pH 7.0.

The purification process starts with recombinant human IL-18BP present in serum free cell culture supernatant from IL-18BP expressing CHO cells, non-filtered, defrosted @ 25° C.

The column was charged with approx. 1-2 mg harvested r-hIL-18BP. The solution was filtered through a 0.45 μm filter before charging the column.

After completion of sample loading, the column was washed with approx. 10 CV PBS, pH 7.0 (1. Wash) and with approx. 10 CV PBS/0.2 NaCl, pH 7.0 (2. Wash). These fractions (FT) were discarded, since they contained only cell culture impurities.

Elution was started with 5CV PBS/0.5 NaCl/50% ethylene glycol. r-hIL-18BP eluted as a main peak. A typical elution profile is shown in FIG. 1.

After completion of the elution, the column was flushed and sanitized with 5 CV of regeneration buffer containing 30% isopropyl alcohol and 0.2M NaOH.

General Affinity Chromatography Conditions:
Temperature: 16-25° C. (RT) or 4° C.

| Ligand | Ligands #1-7 |
|---|---|
| Bed height | 1 ml fritted, gravity-fed |
| Equilibration | 15 CV PBS, pH 7.0 |
| Load | Clarified harvest filtered with 0.45 μm |
| Wash1 | 10 CV PBS, pH 7.0 |
| Wash 2 | 10 CV PBS/0.2 NaCl, pH 7 |
| Elution | PBS/0.5 NaCl/50% ethylene glycol |
| Regeneration and sanitization | 30% isopropyl alcohol/0.2 M NaOH |

Analysis of the Purified Protein
1. Elisa (of load, flow through and eluate)
2. SDS-PAGE/CB (of flow through and eluate)
3. SDS-PAGE/WB (of flow through and eluate)
4. Bradford analysis (of load, flow through and eluate)

Analysis of flow through and eluate fractions revealed pure protein bands at 55-66 kDa in the eluate on SDS-PAGE gels. IL18BP protein of high purity was obtained with affinity ligands of the following structures:

Ligand #1
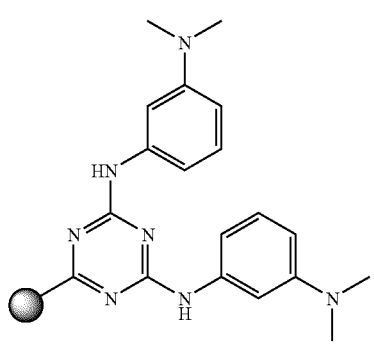

Ligand #2
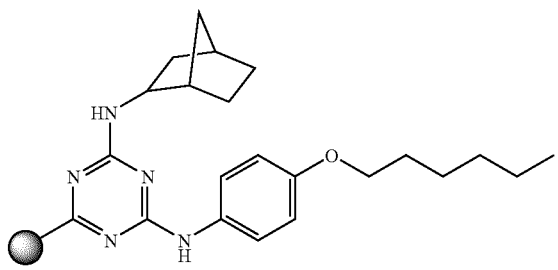

Ligand #3
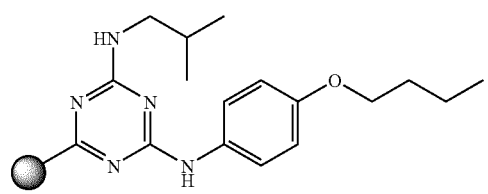

Ligand #4
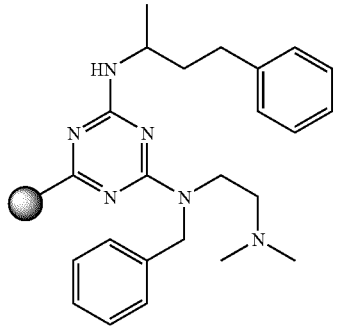

Ligand #5
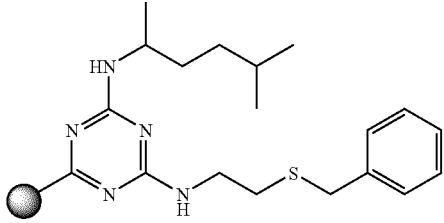

Ligand #6
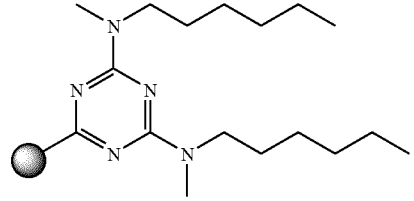

Ligand #7
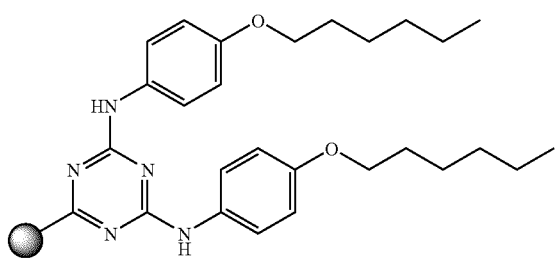

FIG. 2 summarizes recoveries and purities of fractions from chromatography runs with affinity ligands #2, #5, #6 and #7. Protein content was determined by HPLC.

Western blots indicated that the combined eluate and elution tail fractions exhibited a purity of over 80% using affinity ligands #2, #6, and #7. Ligand #6 and #7 showed a preferred selectivity for elution of IL-18BP monomer over dimer and aggregated forms (results not shown).

FIG. 3 summarizes in a table the influence of different washing and elution buffers on the yields of total recovered IL-18BP protein, its monomeric form and its dimeric form. The purification was carried out with affinity ligand #6.

EXAMPLE 2

Purification of Recombinant, Human IL-18BP from Serum-Free CHO Cell Supernatant

Affinity columns, comprising immobilized affinity ligands according to formulae (I) or (II) were used for purification purposes.

The affinity ligand was attached to a matrix as outlined in synthetic scheme 1. The column was packed with the synthesized affinity column material following general instructions for commercial affinity chromatography material and once run blank before use.

The column was equilibrated with 5 BV (bed volumes) of phosphate Na buffer 50 mM+$Na_2SO_4$ 1.2M, pH 5.5, conductivity 103 mS/cm.

The purification process starts with recombinant human IL-18BP present in serum free cell culture supernatant from IL-18BP expressing CHO cells, non-filtered, defrosted @ 25° C.

The column was charged with approx. 1.55 mg harvested r-hIL-18BP+$Na_2SO_4$ 1.2M, whereby the pH was adjusted to 5.5 with phosphoric acid ($H_3PO_4$). The solution was filtered through a 0.45 μm filter before charging the column.

After completion of sample loading, the column was flushed with approx. 10 BV phosphate Na buffer 50 mM+$Na_2SO_4$ 1.2M, pH 5.5, conductivity 103 mS/cm. These fractions (FT) were discarded, since they contained only cell culture impurities.

The column was washed with a buffer containing a mixture sodium phosphate and sodium sulfate.

Elution was started with Na phosphate buffer 50 mM+propylene glycol 35%, pH 7, conductivity 70 mS/cm. r-hIL-18BP eluted as a main peak. A typical elution profile is shown in FIG. 1.

After completion of the elution, the column was flushed and sanitized with 3 BV of regeneration buffer containing 1,6-hexanediol 50%/NaOH 1M.

The column can be stored in 10 mM sodium hydroxide at room temperature until use for the next cycle.

General Affinity Chromatography Conditions:
Temperature: 16-25° C. (RT),

| Ligand | Ligand #6 |
|---|---|
| IL-18 BP loading capacity | 14 g/l |
| Bed height | at least 12 cm |
| Equilibration | 230 cm/h; 5 BV; phosphate Na 50 mM + $Na_2SO_4$ 1.2 M/pH 5.5/cond. 103 mS/cm |
| Load | 53 cm/h, Harvest + 1.2 M $Na_2SO_4$, filtered with 0.45 μm and pH adjusted to 5.5 with $H_3PO_4$ |
| Wash | 53 cm/h; 10 BV ou < 100 mAU phosphate Na 50 mM + $Na_2SO_4$ 0.6 M/pH 5.5/cond: 70 mS/cm |
| Elution | 230 cm/h; 7 BV; phosphate Na 50 mM + propylene glycol 35%/pH 7 |
| Regeneration and sanitization | –230 cm/h, 1,6-hexanediol 50%/NaOH 1 M, flux inverse; 3 BV<br>–4 hs contact<br>–230 cm/h, WFI; 3 BV |
| Stockage | 230 cm/h, NaOH 10 mM; 3 BV |

The average of two purification runs yielded IL-18BP, with a purity of 87% according to Bradford (HCP 30000 ppm). The recovery of monomer was 97% of the starting material.

REFERENCES

1. Altschul S F et al, J Mol Biol, 215, 403-410, 1990
2. Altschul S F et al, Nucleic Acids Res., 25:389-3402, 1997
3. Devereux J et al, Nucleic Acids Res, 12, 387-395, 1984
4. Grantham et al., Science, Vol. 185, pp. 862-864, 1974
5. Kim S. et al., Proc Natl Acad Sci USA 2000, 97, 1190-1195.
6. Novick, D. et al., Immunity 10, 127-136, 1999.
7. Pearson, Methods Enzymol, 183, 63-98, 1990.
8. Puren et al., Proc Natl Acad Sci USA., 96(5), 2256-61, 1999.
9. Urushihara, J Pediatr Surg. 35, 446-, 2000.
10. Vigers et al., Nature. 386 (6621)190-4, 1997.
11. WO 99/09063
12. WO 01/07480
13. WO 01/62285
14. WO 01/85201
15. WO 02/060479
16. WO 02/096456
17. WO 03/080104
18. WO 02/092008
19. WO 02/101049
20. WO 03/013577
21. WO 92/13095
22. WO 01/03737
23. U.S. Pat. No. 4,959,314
24. U.S. Pat. No. 4,588,585
25. U.S. Pat. No. 4,737,462
26. U.S. Pat. No. 5,116,943
27. U.S. Pat. No. 4,965,195
28. U.S. Pat. No. 4,879,111
29. U.S. Pat. No. 5,017,691
30. U.S. Pat. No. 4,904,584

The invention claimed is:

1. A method for the production of purified interleukin-18 binding protein (IL-18BP) comprising:

culturing mammalian host cells expressing recombinant human IL-18BP into a cell culture supernatant, collecting said cell culture supernatant containing recombinant human IL-18BP and contacting it with an affinity chromatography matrix comprising an affinity ligand selected from the group consisting of

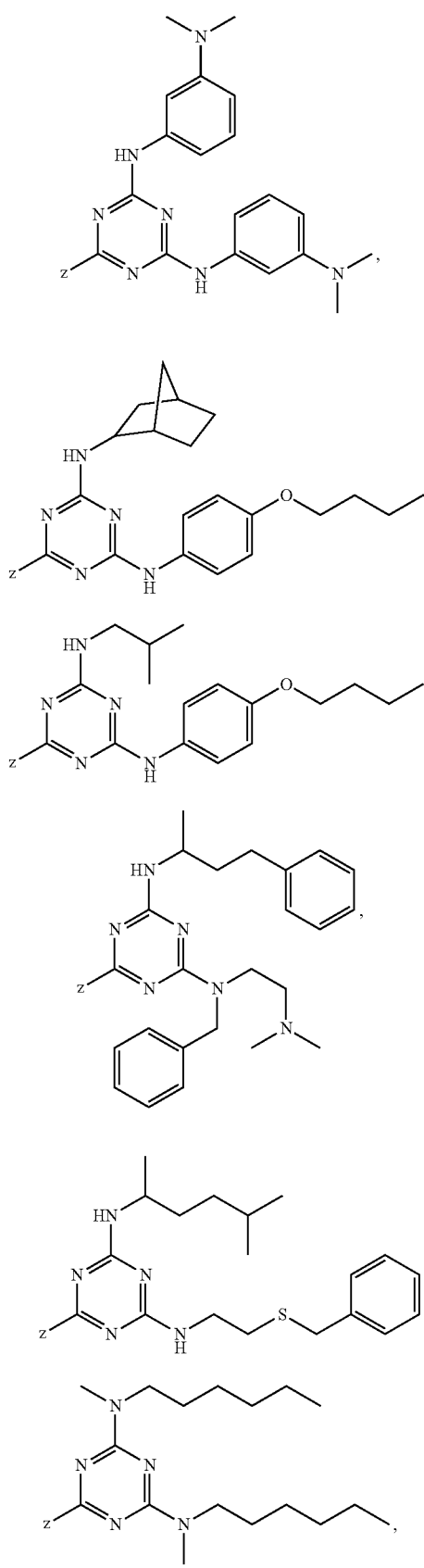

wherein z comprises an amine, azide or hydroxyl group through which said affinity ligand is bound to said affinity chromatography matrix, allowing said recombinant human IL-18BP to bind to the affinity ligand attached to said affinity chromatography matrix; and eluting said recombinant human IL-18BP from said affinity ligand to purify said recombinant human IL-18BP using an eluent comprising phosphate buffered saline (PBS) and propylene glycol at pH 7.

2. The method according to claim 1, wherein said affinity ligand is bound to agarose.

3. The method according to claim 1, wherein the method is carried out at room temperature.

4. The method according to claim 1, further comprising a chromatography step selected from the group consisting of hydrophobic interaction chromatography, reverse phase chromatography and anionic exchange chromatography.

5. The method according to claim 1, wherein said method comprises one or more virus removal steps.

6. The method according to claim 1, wherein the supernatant is serum-free cell culture supernatant.

7. The method according to claim 1, wherein said cell culture supernatant is filtered through a 0.45 μm filter prior to loading onto a column containing said affinity chromatography matrix.

8. The method according to claim 1, wherein said recombinant human IL-18BP is recombinant human IL-18BP isoform a.

9. The method according to claim 1, wherein said recombinant human IL-18BP is recombinant human IL-18BP isoform c.

10. The method according to claim 1, wherein said affinity ligand is

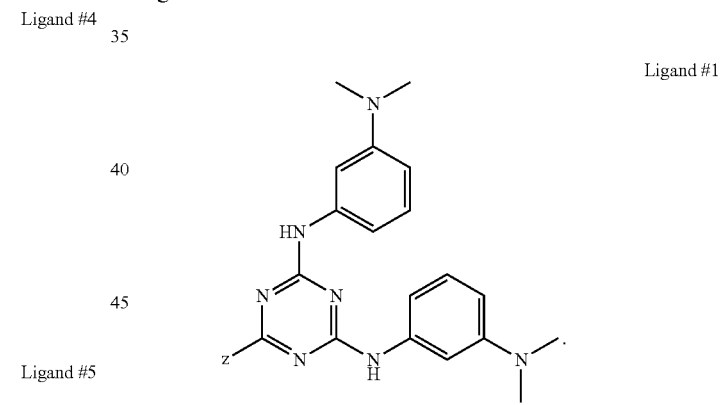

11. The method according to claim 1, wherein said affinity ligand is

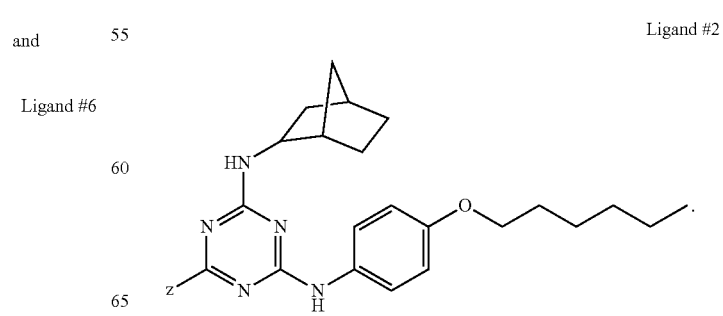

12. The method according to claim 1, wherein said affinity ligand is
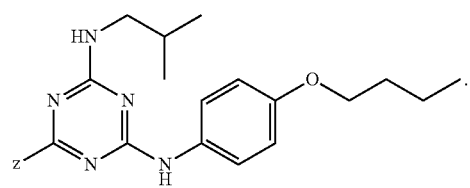
Ligand #3
13. The method according to claim 1, wherein said affinity ligand is
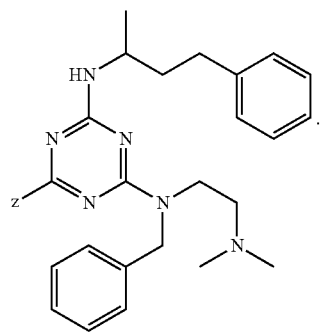
Ligand #4
14. The method according to claim 1, wherein said affinity ligand is
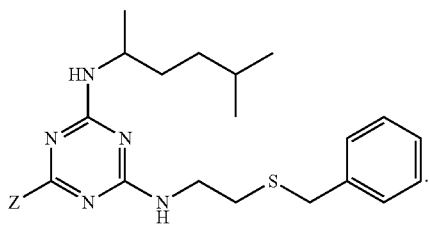
Ligand #5
15. The method according to claim 1, wherein said affinity ligand is
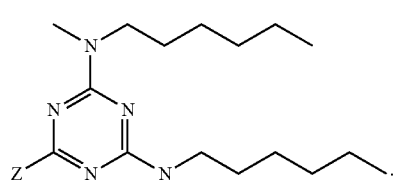
Ligand #6
\* \* \* \* \*

UNITED STATES PATENT AND TRADEMARK OFFICE
CERTIFICATE OF CORRECTION

PATENT NO. : 8,217,152 B2
APPLICATION NO. : 11/916087
DATED : July 10, 2012
INVENTOR(S) : Claire Le Strat et al.

It is certified that error appears in the above-identified patent and that said Letters Patent is hereby corrected as shown below:

Column 3,
Line 31, "chromatrography" should read --chromatography--.
Line 59, "IL-1 with" should read --IL-1β with--.

Column 4,
Line 61, "(IL18BP" should read --(IL-18BP--.
Line 61, "total IL18BP" should read --total IL-18BP--.

Column 5,
Lines 11-12, "aryl include" should read --aryl includes--.

Column 7,
Lines 54-55, "capable for forming" should read --capable of forming--.

Column 9,
Line 51, "ethylendiamine" should read --ethylenediamine--.

Column 11,
Line 46, "used for bind to" should read --used to bind to--.
Line 52, "sulphate" should read --sulfate--.
Line 57, "sulphate" should read --sulfate--.

Column 12,
Line 31, "unspecificly" should read --unspecifically--.
Line 64, "step" should read --steps--.

Column 13,
Line 2, "comprises" should read --comprises:--.
Line 19, "invention, IL-18BP to be" should read --invention, the IL-18BP to be--.

Signed and Sealed this
Twenty-ninth Day of January, 2013

David J. Kappos
*Director of the United States Patent and Trademark Office*

CERTIFICATE OF CORRECTION (continued)
U.S. Pat. No. 8,217,152 B2

Line 34, "If IL-18BP" should read --If the IL-18BP--.

Column 17,
Line 65, "Polyethlyenglycol" should read --Polyethyleneglycol--.

Column 18,
Lines 45-48, "HPLC. Purified IL-18BP may also be defined as moving as a single peak
    in HPLC.
        The"
should read --HPLC.
        The--.

Column 19,
Lines 31-32, "polyethylenglycol" should read --polyethyleneglycol--.

Column 20,
Line 50, "the meaning a range" should read --the meaning and range--.

Column 23,
Lines 40-41, "a mixture sodium" should read --a mixture of sodium--.

Column 26,
Lines 20-21, "the supernatant" should read --the cell culture supernatant--.